United States Patent

Speck et al.

[11] 4,283,381
[45] Aug. 11, 1981

[54] TRIIODINATED AMINOACETAMIDO ISOPHTHALAMIDE X-RAY CONTRAST AGENTS

[75] Inventors: Ulrich Speck; Erich Klieger; Wolfgang Mützel, all of Berlin, Fed. Rep. of Germany

[73] Assignee: Schering Aktiengesellschaft, Berlin, Fed. Rep. of Germany

[21] Appl. No.: 167,597

[22] Filed: Jul. 11, 1980

[30] Foreign Application Priority Data

Jul. 12, 1979 [DE] Fed. Rep. of Germany ....... 2928417

[51] Int. Cl.$^3$ .................. A61K 49/04; C07C 103/183; C07C 103/50
[52] U.S. Cl. ................................. 424/5; 260/326 N; 260/501.16; 260/501.18; 564/153
[58] Field of Search ........................... 564/153; 424/5; 260/501.16, 501.18

[56] References Cited

U.S. PATENT DOCUMENTS

| | | | |
|---|---|---|---|
| 2,776,241 | 1/1957 | Priewe et al. ............................ | 424/5 |
| 3,178,473 | 4/1965 | Holtermann et al. .............. | 424/5 X |
| 3,701,771 | 10/1972 | Almen et al. ....................... | 424/5 X |
| 3,953,501 | 4/1976 | Klieger et al. ...................... | 424/5 X |
| 4,021,481 | 5/1977 | Almen et al. ....................... | 424/5 X |
| 4,192,859 | 3/1980 | Mackaness et al. ..................... | 424/5 |

OTHER PUBLICATIONS

J. Ackerman, Chem. Abstracts 72:66642d (1970).

Primary Examiner—Thomas A. Waltz
Attorney, Agent, or Firm—Millen & White

[57] ABSTRACT

Compounds of the formula

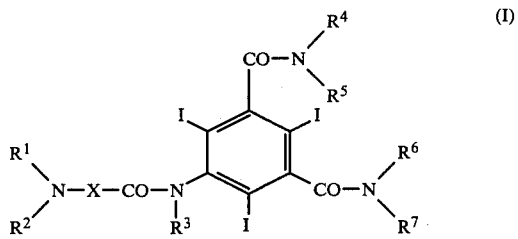

(I)

wherein
X is alkylene, optionally substituted by hydroxy, methoxy or amino;
$R^1$ is hydrogen or $C_{1-4}$ alkyl;
$R^2$ is hydrogen, $C_{1-4}$ alkyl, or $C_{2-4}$-alkyl substituted by 1–3 OH groups;
$R^3$ is hydrogen, $C_{1-4}$ alkyl, or $C_{2-4}$-alkyl substituted by 1–3 OH groups;
$R^4$ is hydrogen, $C_{1-4}$-alkyl, or $C_{2-4}$-alkyl substituted by 1–3 OH groups;
$R^5$ is $C_{2-4}$-alkyl substituted by 1–3 OH groups;
$R^6$ is hydrogen, $C_{1-4}$-alkyl or $C_{2-4}$-alkyl substituted by 1–3 OH groups; and
$R^7$ is $C_{2-4}$-alkyl substituted by 1–3 OH groups,
or a salt thereof with an acid
are useful as opaquing agents in x-ray contrast media.

12 Claims, No Drawings

TRIIODINATED AMINOACETAMIDO ISOPHTHALAMIDE X-RAY CONTRAST AGENTS

BACKGROUND OF THE INVENTION

The present invention relates to new triiodoisophthalic acid derivatives useful as opaque agents in x-ray contrast media.

For the complete roentgenological visualization of, for example, essential portions of the vascular system for instance, the aorta, or for the complete representation of the urinary tract system, contrast agent solutions must be administered in high concentrations to obtain satisfactory contrast in the system to be examined. Such high contrast medium concentrations, in turn, require that the contrast agents possess a very high water solubility with simultaneously low toxicity and good compatibility.

It is known that the general compatibility of x-ray contrast media depends on their hydrophilic character (P. K. Knoefel, Radiocontrast Agents, Vol. Pergamon Press [1971]: 133 et seq.). Moreover, it is known that the electrical charge of the cation and anion contributes substantially to a reduction of the lipophilic-toxic effects, expecially of the triiodinated aromatics.

In the presently used x-ray contrast medium salt solutions, the anion is the iodine-containing, opaquing components. The cation does not play any role in the forming of the x-ray radiographs. On the contrary, a number of undesirable effects ensue from their presence.

For example, all ions contribute toward the osmotic pressure of the x-ray contrast medium salt solutions in proportion to their molar concentrations, e.g., in the salts of substituted triiodobenzoic acids, half of the osmotic pressure originates from the iodine-free and thus contrast-ineffectual cation. The high osmotic pressure of concentrated x-ray contrast medium solutions is responsible for a number of undesirable pharmacological effects, such as vasodilation, pain, as well as a diuretic effect and thus a dilution of the excreted contrast medium in urography. Furthermore, the customary cations derived from iodine-free bases of high molecular weight, such as, meglumine, glucamine, lysine, arginine, and others, considerably raise the viscosity of the contrast medium solutions.

Cations having a lower molecular weight increase the viscosity of the contrast medium solutions to only a slight extent, but, on the other hand, have a toxic effect. Thus, it is known that there is damage to the blood-brain barrier and triggering of vascular pain by Na+ ions, and a higher toxicity of ethanolamine (EVILL, C. A. and G. T. BENNESS: Metrizamide as a Non-Ionic Urographic Agent, A Comparison with Sodium Iothalamate and Its Dimer, Invest. Radiol. 9: 434–437 [1974]; S. I. HILAL: Trends in Preparation of New Angiographic Contrast Media with Special Emphasis on Polymeric Derivatives, Invest. Radiol. 5: 458–468 [1970]).

SUMMARY OF THE INVENTION

It is thus an object of this invention to provide compounds useful as opaquing agents in contrast media, which are suitable for cation formation, possessing, on the one hand, the advantages of the comparable compounds heretofore used for cation formation and, on the other hand, avoiding the disadvantages of these comparable compounds.

Upon further study of the specification and appended claims, further objects and advantages of this invention will become apparent to those skilled in the art.

In one aspect of this invention, these objects have been attained by providing suitable bases which are 2,4,6-triiodoisophthalic acid derivatives and which exhibit the required low toxicity and are suitable for forming readily water-soluble salts with contrast medium acids.

Especially suitable are the novel compounds of Formula I

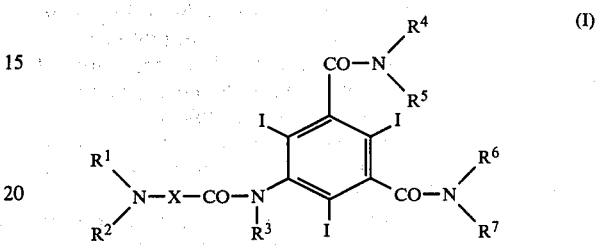

wherein
X is lower alkylene,
$R^1$ is hydrogen or lower alkyl,
$R^2$ is hydrogen or an optionally hydroxylated lower alkyl,
$R^3$ is hydrogen or an optionally hydroxylated lower alkyl,
$R^4$ is hydrogen or an optionally hydroxylated lower alkyl,
$R^5$ is lower mono- or polyhydroxyalkyl,
$R^6$ is hydrogen or optionally hydroxylated lower alkyl, and
$R^7$ is lower mono- or polyhydroxyalkyl, and the salts thereof with contrast medium acids.

DETAILED DISCUSSION

The compounds of this invention are distinguished by the following properties inter alia. The electrical charge is preserved in its role as a carrier of hydrophilic properties and as a cause for the extraordinarily good solubility of the triiodoaromatics. The osmotic pressure of the contrast medium solutions is significantly reduced because the proportion of osmotic pressure stemming from the nonopaquing cation is eliminated. Their viscosity is significantly reduced, since with the same iodine concentration, the salt concentration is considerably lowered. This permits production of highly concentrated and yet very low viscosity solutions. A lower viscosity facilitates the administration of the solutions and has a favorable effect in selective angiography insofar as microcirculation is less impaired than by viscous solutions.

All the lower alkyl groups of the compounds of this invention can be straight chain or branched and contain 1–4 carbon atoms. Methyl is preferred. However, likewise suitable are alkyl groups, such as, for example, ethyl, n-propyl or isopropyl.

When these are hydroxy-substituted, they can also be straight-chain or branched. They generally contain 2–4, preferably 2–3 carbon atoms and 1–3, preferably 2 hydroxy groups in the alkyl residue. Suitable hydroxyalkyl residues include, for example: 2-hydroxypropyl, 3-hydroxpropyl, 1-(hydroxymethyl)ethyl, 2,3-dihydroxybutyl, 2,4-dihydroxybutyl, 3,4-dihydroxybutyl, 2,3-dihydroxymethylpropyl, (trishydroxymethyl)- methyl, 2,3,4-trihydroxybutyl, 1,3,4-trihydroxybutyl, etc., and preferably 2-hydroxyethyl, 1,3-dihydroxyisopropyl and 2,3-dihydroxypropyl.

The aminoacyl residue $R^1R^2.N$-X-CO- ($R^1$ and $R^2$ being as defined above) as derived from conventional, synthetic and natural amino acids. Thus, insofar as these do not fall within the literal confines of the foregoing definitions or the appended claims, such residues are equivalents thereof, as are the corresponding overall compound equivalents of the compounds of this invention. Therefore, X can be a straight-chain or branched alkylene residue, e.g., of 1–5 C atoms which can optionally be substituted by a hydroxy, methoxy or amino group. Preferred residues X include straight-chain or branched, lower alkylene residues of 1–4, especially 1–2 carbon atoms, e.g. methylene, ethylene, propylene, butylene, methylmethylene, methylethylenes, methylpropylene, methylbutylene, ethylpropylene, hydroxyethylene, hydroxymethylmethylene, methoxymethylmethylene, etc.

The compounds of this invention can also be utilized, in particular, for converting x-ray contrast medium acids into the salts thereof.

For salt formation, essentially all known, intravenously administrable acids useful as opaquing agents in contrast media are suitable. The iodine-containing contrast medium acids presently customary for uro- and angiography and for the visualization of body cavities may be mentioned as being preferred, such as, for example, mononuclear, triiodinated benzoic acids, e.g. amidotrizoic acid, iodamide, iothalamic acid, ioxithalamic acid, ioglicinic acid, and others as well as binuclear hexaiodinated dicarboxylic acids, e.g. iocarmic acid, and others.

The salts of this invention, consisting of a triiodinated cation of this invention and a conventional, iodinated contrast medium acid anion, are distinguished by the stability characteristic of salt solutions and by an excellent compatibility, as can be seen from the following table, using as examples 5-aminoacetamido-2,4,6-triiodoisophthalic acid bis(2-hydroxyethyl)amide iothalamate (A-Iothalamate) of this invention and 5-amidoacetamido-2,4,6-isophthalic acid bis(N-methyl-2,3-dihydroxypropyl) diamide amidotrizoate (B-Amidotrizoate) of this invention.

TABLE I

| | A-Iothal-amate | Na-Iothal-amate | Megl. Iothal-amate | B-Amido-tri-zoate | Megl. Amido-tri-zoate |
| --- | --- | --- | --- | --- | --- |
| Iodine content of salt | 58% | 60% | 47% | 54% | 47% |
| Viscosity of solution with 300 mg iodine/ml, 37° C. in centipoises | 2.4 | 2.7 | 5.2 | 3.5 | 5.0 |
| Molarity of solution with 300 mg iodine in mole/liter | 0.394 | 0.787 | 0.787 | 0.394 | 0.787 |
| $LD_{50}$ Mouse (20 g) g iodine/kg | ≧10.5 | 8.0 | 4.5 (4.1–4.9) | — | — |
| $LD_{50}$ Rat (100 g) g iodine/kg | ≧10 | 7.0 | 7.4 (6.8–7.9) | ≧10 | 7.5 |

$LD_{50}$ on mice and rats was determined after intravenous injection of the solutions containing 300 mg iodine/ml with an injection rate of 2 ml/min.

The above table shows, using as an example the iothalamate salt of this invention, that the novel compounds are distinguished by an especially high iodine content which is otherwise attained only by the less well compatible sodium salts. Furthermore, it can be seen that the viscosity of a solution of the salts according to this invention is especially low, and that the molarity and thus the osmotic pressure of the salt solution is substantially lower than the molarity and osmotic pressure of corresponding sodium and meglumine salt solutions. Also, compatibility of the compounds of this invention in mice and rats is clearly better than that of the conventional sodium or meglumine salts.

The excellent compatibility of the novel salts, in conjunction with their low viscosity, makes it possible to produce highly concentrated and yet readily injectable x-ray contrast medium solutions.

In general, the opaquing substances of this invention can be used in contrast media solutions.

In general, the opaquing substances of this invention can be used in contrast media solutions in concentrations of 50–400 mg I/ml of solution, and dosages of 5–500 ml. In the form of their salt solutions, they can be used especially in concentrations of 20–500 mg iodine per milliliter of solution, and dosages of 2–500 ml.

Because of their good pharmacological properties, the novel compounds of this invention are excellently suitable as opacifying compounds in all fields of application of water soluble x-ray contrast media, especially for intravasal, subarachnoid and various local applications in the same manner as known x-ray contrast agents, e.g., metrizamide.

The present invention therefore also relates to novel x-ray contrast media based on the compounds of Formula I.

Such novel x-ray contrast media can be prepared in a conventional manner, for example, by bringing the opacifying compound into a form suitable for intravenous administration, together with additives conventional in galenic pharmacy, e.g., stabilizers, such as sodium edetate, calcium disodium edetate, physiologically compatible buffers, sodium chloride, and similar compounds.

The compounds of this invention can be employed in mixture with conventional excipients, i.e., pharmaceutically acceptable organic or inorganic carrier substances suitable for parenteral or enteral application which do not deleteriously react with the active compound, for administration to a patient, e.g., mammals including humans. Suitable pharmaceutically acceptable carriers, include but are not limited to, water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For intravenous administration, generally, the amount of active agent per unit dosage is about 1 to 80 g, preferably 2 to 70 g.

The particular concentration and dosage of the novel x-ray contrast compound of this invention in an aqueous medium is entirely dependent on the method of x-ray diagnostics employed.

The present invention furthermore relates to a process for producing the compounds of this invention, comprising, conventionally, (a) reacting a compound of Formula II

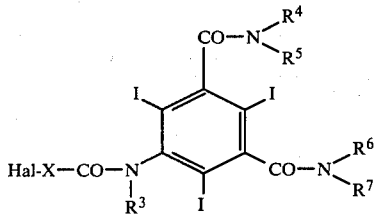

wherein
R³ through R⁷ and X are as defined above and
Hal is chlorine or bromine, with an amine of Formula III

wherein R¹ and R² are as defined above or (b) conventionally hydrazinolizing a compound of Formula IV

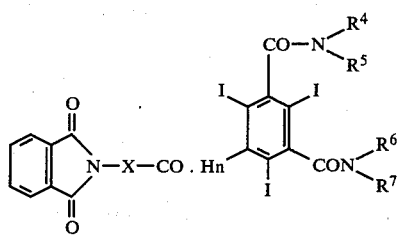

wherein X and R⁴-R⁷ are as defined above and, optionally, subsequently N-alkylating the thus-obtained bases, optionally with intermediary blockage of free hydroxy groups and/or converting it to its salt with an x-ray contrast medium acid.

The reaction of the starting compound of Formula II with the amine of Formula III (process version a) takes place according to conventional methods in the presence of a suitable solvent at 0°–100° C., preferably 0°–60° C. The reaction temperature is essentially determined by the physical properties of the amine employed. If the amine is readily volatile, the reaction is advantageously conducted at room temperature or also below room temperature. If the amine utilized is less volatile, the reaction can also be effected at a higher reaction temperature. Suitable solvents include, in particular, polar solvents, e.g. water, dioxane, dimethylformamide, dimethylacetamide, lower alcohols, such as methanol, ethanol, isopropanol, etc., and mixtures thereof.

Compounds of Formula I wherein R¹ and R² are both hydrogen can be advantageously obtained according to process version (b) from compounds of Formula IV by hydrazinolysis. The hydrazinolysis is conducted according to generally conventional methods (see, for example, DOS [German Unexamined Laid-Open Application] No. 2,523,567; J. Am. Chem. Soc. 71:1856 [1949]; J. Chem. Soc. 2343, 1926; Chem. Ber. [Chemical Reports] 83:244 [1950]). For this purpose the starting compound of Formula IV is dissolved, for example, in an organic, preferably water-miscible solvent (e.g. methanol or ethanol) and is reacted with hydrazine in a preferably alcoholic solution, wherein the hydrazine is suitably used in excess.

The subsequent introduction of an alkyl or a hydroxysubstituted alkyl group R³ is likewise accomplished according to N-alkylating methods known per se to those skilled in the art, for example by conducting the reaction in an alkaline solution with the corresponding alkyl sulfate or alkyl halogenide, preferably bromide, at room temperature.

If it is advantageous during the reaction to intermediarily block any free hydroxy groups present in the molecule before the N-alkylation, this is effected according to conventional methods by incorporating readily cleavable groups. The introduction of such blocking groups can take place, for example, by esterification (e.g. introduction of preferably an acetyl or benzyl residue) or by etherification (e.g. introduction of the triphenylmethyl residue). The blocking of the hydroxy groups can also be achieved by ketalization or acetalization, e.g. by means of acetaldehyde, acetone or dihydropyran.

The subsequent splitting off of the intermediarily introduced blocking groups with liberation of the finally desired hydroxy groups likewise takes place according to methods generally known to those skilled in the art. Thus, the step of splitting off the blocking groups can be conducted without a separate reaction stage, e.g., during the working up and isolating of the reaction products. However, it is also possible to effect this reaction in the usual way in a separate reaction stage. Acyl blocking groups can be split off, for example, by alkaline hydrolysis, and acetal, ketal, or ether blocking groups can be split off by acid hydrolysis.

The salts of this invention can also be prepared in a conventional way, for example by reacting the iodinecontaining, organic acid with the base in water in equivalent weight proportions. The salts of this invention can be isolated from the aqueous solution by the usual methods, such as, for example by removing the solvent by evaporation, or by precipitation using organic solvents.

The novel starting compounds of Formula II or IV are suitably prepared from the known 5-amino- and 5-alkylamino-2,4,6-triiodoisophthalic acid dichlorides (alkyl=CH₃ or C₂H₅), respectively, in accordance with methods known per se, e.g, per the following.

In the first reaction step the 5-(R³-amino)-2,4,6-triiodoisophthalic acid dihalogenide is N-acylated in a conventional way with the corresponding halo-fatty acid chloride Hal.X.COCl (wherein Hal and X have the meanings given above).

In the second reaction step the amidation of the two carboxy groups is then conducted by reacting the acid chloride with NH.R⁴R⁵ or HN.R⁶R⁷ according to conventional methods. Thus, the two amidation reactions take place, for example, in a suitable solvent at 0°–100 C., preferably at 20°–80° C. Suitable solvents are, inter alia, polar solvents, such as water, dioxane, tetrahydrofuran, dimethylformamide, dimethylacetamide, hempa, and similar solvents, and the mixtures thereof. Since the amidation reaction takes place exothermally, it is in some cases advantageous to slightly cool the reaction mixture to be able to maintain the reaction temperature at about 50° C. to 60° C. The hydrogen chloride liberated during the amidation reaction is bound either by a corresponding excess of base HN.R⁴R⁵ or NH.R⁶R⁷ or by adding a customary proton acceptor. Advantageous proton acceptors are tertiary amines, such as, for example, triethylamine, tributylamine, or pyridine.

The inorganic or organic salts obtained during the course of the reaction are conventionally separated, advantageously, for example, with the aid of customary ion-exchange columns or by filtration over conventional adsorbents, such as "Diaion" or "Amberlite" XAD-2 and 4.

The preparation of the starting compound of Formula II will be described in detail, using as an example the production of 5-chloroacetamido-2,4,6-triiodoisophthalic acid bis(N-methyl2,3-dihydroxypropyl)diamide:

At maximally 10° C., 67.7 g (0.6 mol) of chloroacetyl chloride is added dropwise under agitation within 20 minutes to a solution of 119.1 g (0.2 mol) of 5-amino-2,4,6-triiodoisophthalic acid dichloride in 400 ml of dimethylacetamide; the mixture is further stirred for 1 hour under ice cooling and then overnight at room temperature. The reaction mixture is then treated with 6 l of water, the thus-produced precipitate is vacuum-filtered and dissolved in 3.5 l of ethyl acetate. The ethyl acetate solution is washed neutral with 400 ml of saturated NaHCO$_3$ solution and twice with water, dried with Na$_2$SO$_4$, and concentrated under vacuum. The residue is treated with 800 ml of ether and dried under vacuum at 50° C., thus obtaining 100.8 g (75% of theory) of 5-chloroacetamido-2,4,6-triiodoisophthalic acid dichloride, m.p. 254°–256° C. (decomposition).

Under agitation, 322.3 g (3.07 mol) of N-methylaminopropane-2,3-diol in 1.46 l of dioxane is added dropwise at room temperature within 40 minutes to a solution of 490.7 g (0.74 mol) of 5-chloroacetamido-2,4,6-triiodoisophthalic acid dichloride in 5.8 l of dioxane; the mixture is then further stirred overnight. Then the solvent is distilled off, the residue is washed twice with dioxane, dissolved in 1.1 l of water, and filtered over a cation exchanger and an anion exchanger. After treatment of the aqueous fraction with activated carbon, the product is concentrated under vacuum, and the residue is dried at 50° C. under vacuum, thus obtaining 396 g (67%) of 5-chloroacetamido2,4,6-triiodoisophthalic acid bis(N-methyl-2,3-dihydroxypropyl)diamide, m.p.~290° C. (decomposition).

The starting compound of general Formula IV is also prepared from 5-(R$^3$-amino)-2,4,6-triiodoisophthalic acid dichloride by acylation of the 5-positioned aromatic amino group with the corresponding N-phthaloyl-X-COCl (X having the above-indicated meanings) in accordance with conventional methods, and by subsequent amidation of the acid chloride groups in the 1- and 3-positions as described above. In detail, the preparation of the starting compound of general Formula IV will be described below, using as an example the production of 2,4,6-triiodo-5-phthalimidoacetamidoisophthalic acid bis(N-methyl-2,3-dihydroxypropyl)diamide:

Under agitation, 178.9 g of N-phthaloylglycine chloride is added in incremental portions to an ice-cooled solution of 119.1 g (0.2 mol) of 5-aminoisophthalic acid dichloride in 0.5 l of dimethylacetamide; the mixture is stirred for several hours under ice cooling and then overnight at room temperature. Then the reaction solution is gradually stirred into about 10 l of water, agitated for 45 minutes, the precipitate vacuum-filtered, and the latter washed with water and taken up in 3 l of ethyl acetate.

The filtered ethyl acetate phase is washed with half-saturated sodium bicarbonate solution and twice with water, dried with sodium sulfate, and concentrated under vacuum. The residue is then treated with ether and dried under vacuum at 50° C., thus obtaining 127.3 g (81%) of 2,4,6-triiodo-5-phthalimidoacetamidoisophthalic acid dichloride, m.p.~255° C. (decomposition).

Under agitation, a solution of 31.5 g of N-methylaminopropane-2,3-diol in 0.15 l of dimethylacetamide is gradually added dropwise to a solution, heated to 50° C., of 78.3 g (0.1 mol) of 2,4,6-triiodo-5-phthalimidoacetamidoisophthalic acid dichloride in 0.25 l of dimethylacetamide. After the exothermal reaction has ceased, 71.3 ml of tributylamine is added, and the mixture is stirred for another hour at 50° C. After cooling to room temperature, the solution is concentrated under vacuum, the residue is treated for 1 hour with 2 l of methylene chloride, the precipitate is separated, washed with methylene chloride, again aftertreated with 2 l of methylene chloride, and the product is vacuum-filtered and dried under vacuum at 50° C. The crude product is then heated with water under agitation, during which step crystallization occurs. After cooling under agitation, the precipitate is vacuum-filtered, washed with water, and dried under vacuum at 50° C., thus obtaining 66.0 g (72%) of 2,4,6-triiodo-5-phthalimidoacetamidoisophthalic acid bis(N-methyl-2,3-dihydroxypropyl)diamide, m.p. 303° C. (decomposition).

According to definition, the substituents —CON.R$^4$R$^5$ and —CON.R$^6$R$^7$ in the compounds of Formula I of this invention can also be different. In this case the amidation of the —COCl groups in the 1- and 3-positions is likewise conducted according to the above-indicated operating methods, but in stages, i.e. first with the base HN.R$^4$R$^5$ and then with the different base HN.R$^6$R$^7$ as will be described in detail, using as an example the preparation of 2,4,6-triiodo-5-phthalimidoacetamidoisophthalic acid [(2,3-dihydroxypropyl)-(N-methyl-2,3-dihydroxypropyl)]diamide:

Under agitation, 156.6 g (0.2 mol) of 2,4,6-triiodo5-phthalimidoacetamidoisophthalic acid dichloride is added to a solution, heated to 60° C., of 42.1 g (0.4 mol) of N-methylaminopropane-2,3-diol in 1 l of dioxane; the mixture is further agitated for 3 hours at 60° C., filtered, and the filtrate concentrated under vacuum. The residue is then stirred for 30 minutes with 2.5 l of water, the separated precipitate is extracted in 3 l of ethyl acetate with respectively 1 l of saturated NaHCO$_3$ solution and 1 l of water, dried with Na$_2$SO$_4$, and concentrated under vacuum. The residue is aftertreated with ether. After drying under vacuum at 50° C., 108.4 g (64%) of 2,4,6-triiodo-5-phthalimidoacetamidoisophthalic acid (N-methyl-2,3-dihydroxypropyl)amide chloride is thus obtained, m.p. 268°–272° C. (decomposition).

Under agitation, 18.2 g of 1-amino-2,3-propanediol in 100 ml of dimethylacetamide is added dropwise to a solution, heated to 60° C., of 68.0 g of 2,4,6-triiodo-5-phthalimidoacetamidoisophthalic acid (N-methyl-2,3-dihydroxypropyl)amide chloride in 1.5 l of dimethylacetamide. The mixture is stirred for 2 hours at 50° C., and the dimethylacetamide is removed under vacuum. The residue is treated twice with methylene chloride, vacuum-filtered, and dried under vacuum at 50° C., thus obtaining 2,4,6-triiodo-5-phthalimidoacetamidoisophthalic acid [(2,3-dihydroxypropyl)-(N-methyl-2,3-dihydroxypropyl)]diamide, yield: 38.3 g (56%), m.p. 286°–289° C. (decomposition).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the following examples are set forth in degrees Celsius.

EXAMPLE 1

5-Aminoacetamido-2,4,6-triiodoisophthalic Acid Bis(N-methyl-2,3-dihydroxypropyl)diamide 50.0 g of 5-chloroacetamido-2,4,6-triiodoisophthalic acid bis(N-methyl-2,3-dihydroxypropyl)diamide (m.p. 290° under decomposition) is stirred in 370 ml of 25% ammonia with the addition of 250 ml of water for 7 days at room temperature. Thereafter the solution is concentrated, distilled several times with water, the residue taken up in 130 ml of water, the solution introduced over an anion exchanger, and the filtrate treated with activated carbon and concentrated under vacuum. After repeating the distillation with water several times, the preparation is dried under vacuum at 50°. Yield: 41.9 g (86%), m.p. ~259° (under decomposition).

The following compounds are prepared analogously:
(a) 5-(Aminoacetamido-N-methyl)-2,4,6-triiodoisophthalic acid bis(N-methyl-2,3-dihydroxypropyl)diamide, yield: 95% of theory, m.p. 235° (under decomposition) from 5-(chloroacetamido-N-methyl)-2,4,6-triiodoisophthalic acid bis(N-methyl-2,3-dihydroxypropyl)diamide, m.p. 305° (decomposition).

(b) 5-Aminoacetamido-2,4,6-triiodoisophthalic acid bis(2,3-dihydroxypropyl)diamide, yield: 68% of theory, m.p. 244°-246° (decomposition) from 5-chloroacetamido-2,4,6-triiodoisophthalic acid bis(2,3-dihydroxypropyl)diamide, m.p. 313° (decomposition).

(c) 5-(Aminoacetamido-N-methyl)-2,4,6-triiodoisophthalic acid bis(2,3-dihydroxypropyl)diamide, yield: 91% of theory, m.p. 235° (decomposition) from 5-(chloroacetamido-N-methyl)-2,4,6-triiodoisophthalic acid bis(2,3-dihydroxypropyl)diamide, m.p. 235° (decomposition).

(d) 5-Aminoacetamido-2,4,6-triiodoisophthalic acid bis(2-hydroxy-1-hydroxymethylethyl)diamide, yield: 81% of theory, m.p. 280° (decomposition) from 5-chloroacetamido-2,4,6-triiodoisophthalic acid bis(2-hydroxy-1-hydroxymethylethyl)diamide, m.p. 300° (decomposition).

(e) 5-(2-Aminopropionamido)-2,4,6-triiodoisophthalic acid bis(2,3-hydroxy-1-hydroxymethylethyl)diamide, yield: 39% of theory, m.p. 278° (decomposition) from 5-(2-chloropropionamido)-2,4,6-triiodoisophthalic acid bis(2,-hydroxy-1-hydroxymethylethyl)diamide, m.p. 314° (decomposition).

(f) 5-(3-Aminopropionamido)-2,4,6-triiodoisophthalic acid bis(N-methyl-2,3-dihydroxypropyl)diamide, m.p. 275° (decomposition) from 5-(3-chloropropionamido)-2,4,6-triiodoisophthalic acid bis(N-methyl-2,3-dihydroxypropyl)diamide, m.p. 252° (decomposition).

(g) 5-(Aminoacetamido-N-methyl)-2,4,6-triiodoisophthalic acid bis(2-hydroxy-1-hydroxymethylethyl)diamide, yield: 57% of theory, m.p. 263° (decomposition) from 5-(chloroacetamido-N-methyl)-2,4,6-triiodoisophthalic acid bis(2-hydroxy-1-hydroxymethylethyl)diamide, m.p. 320° (decomposition).

EXAMPLE 2

2,4,6-Triiodo-5-methylaminoacetamidoisophthalic Acid Bis(N-methyl-2,3-dihydroxypropyl)diamide 40.5 g (0.05 mol) of 5-chloroacetamido-2,4,6-triiodoisophthalic acid bis(N-methyl-2,3-dihydroxypropyl)diamide (m.p. 290°, decomposition) is stirred with 300 ml of 40% aqueous methylamino solution and with the addition of 200 ml of water for 7 days at room temperature. The reaction mixture is worked up as described in Example 1. Yield: 24.2 g (60%), m.p. ~245° (decomposition).

The following compounds are prepared analogously:
(a) 2,4,6-Triiodo-5-methylaminoacetamidoisophthalic acid bis(2,3-dihydroxypropyl)diamide, yield: 73% of theory, m.p. 265° (decomposition) from 5-chloroacetamido-2,4,6-triiodoisophthalic acid bis(2,3-dihydroxypropyl)diamide, m.p. 313° (decomposition).

(b) 2,4,6-Triiodo-5-methylaminoacetamido-N-methylisophthalic acid bis(2,3-dihydroxypropyl)diamide, yield: 67% of theory, m.p. 265° (decomposition) from 5-(chloroacetamido-N-methyl)-2,4,6-triiodoisophthalic acid bis(2,3-dihydroxypropyl)diamide, m.p. 305° (decomposition).

EXAMPLE 3

5-Hydroxyethylaminoacetamido-2,4,6-triiodoisophthalic Acid Bis(2-hydroxyethyl)diamide Under agitation, 36.1 g of 5-chloroacetamido-2,4,6-triiodoisophthalic acid bis(2-hydroxyethyl)diamide (no melting or decomposition up to 320°) is introduced into a solution of 348.9 ml of ethanolamine in 375 ml of methanol, and the mixture is stirred for 48 hours at room temperature. The mixture is then concentrated under vacuum, the oily residue is stirred overnight with 187 ml of water, the precipitate is vacuum-filtered and dried under vacuum at 50°. Yield: 19.5 g (52%), m.p. 242°-244° (decomposition).

EXAMPLE 4

5-Hydroxyethylaminoacetamido-2,4,6-triiodoisophthalic Acid Bis(N-methyl-2,3-dihydroxypropyl)diamide A solution of 40.5 g of 5-chloroacetamido-2,4,6-triiodoisophthalic acid bis(N-methyl-2,3-dihydroxypropyl)diamide (m.p. 290°, decomposition) in 300 ml of methanol is combined with 299.5 ml of ethanolamine; the mixture is stirred for 48 hours at room temperature. Then the solution is concentrated under vacuum, the residue is dissolved in 250 ml of water, the solution is adjusted to pH 7 with dilute hydrochloric acid and filtered for desalting purposes over "Amberlite" XAD-4. After treatment with activated carbon, the salt-free solution is concentrated under vacuum. The residue is dried under vacuum at 50°. Yield: 18.0 g (43%), m.p. about 250° (decomposition).

EXAMPLE 5

5-Aminoacetamido-2,4,6-triiodoisophthalic Acid Bis(2-hydroxyethyl)diamide 50.4 g (50 millimoles) of 5-bromoacetamido-2,4,6-triiodoisophthalic acid bis(bromoacetoxyethylamide) is suspended in 500 ml of 8 N ammonia. After several hours of agitation, the solution is concentrated to dryness under vacuum, combined with 150 ml of water, adjusted to pH 8-9 with dilute ammonia, and stirred for 1-2 days until complete precipitation has occurred. After vacuum-filtering, washing, and drying, the yield of title compound is 25.5 g (72.6% of theory). Decomposition under iodine cleavage starting with 270°.

EXAMPLE 6

5-Aminoacetamido-2,4,6-triiodoisophthalic Acid Bis(N-methyl-2,3-dihydroxypropyl)diamide At room temperature, 18.2 ml of 80% hydrazine hydrate is added dropwise under agitation to a suspension of 92.0 g of 2,4,6-triiodo-5-phthalimidoacetamidoisophthalic acid bis(N-methyl-2,3-dihydroxypropyl)diamide (m.p. ~303°, decomposition) in 600 ml of ethanol, and the mixture is then heated under reflux for 2 hours. After cooling, 300 ml of 1 N hydrochloric acid is added to the reaction mixture. The mixture is thereafter stirred for 1 hour at room temperature, the precipitate is vacuum-filtered, the filtrate is freed of ethanol under vacuum, and the remaining aqueous solution is filtered over an alkaline ion exchanger. The filtrate is then concentrated under vacuum, the residue stirred while heating under reflux with 300 ml of n-butanol, and further stirred at room temperature. The precipitate is vacuum-filtered, aftertreated with cold n-butanol, and dried under vacuum at 50°. Yield: 62.4 g (79% of theory), m.p. ~263° (decomposition).

Analogously, the following compounds are prepared:

(a) 5-Aminoacetamido-2,4,6-triiodoisophthalic acid [(2,3-dihydropropyl)-(N-methyl-2,3-dihydroxypropyl)-]diamide, m.p. 251° (decomposition) from 2,4,6-triiodo-5-phthalimidoacetamidoisophthalic acid [(2,3-dihydroxypropyl)-(N-methyl-2,3-dihydroxypropyl)]diamide, m.p. 286°-289° (decomposition).

(b) 5-(2-Aminopropioniamido)-2,4,6-triiodoisophthalic acid bis(2,3-dihydroxypropyl)diamide, yield: 49% of theory, m.p. 248° (decomposition) from 2,4,6-triiodo-5-phthalimidopropionamidoisophthalic acid bis(2,3-dihydroxypropyl)diamide, m.p. ~298° (decomposition).

(c) 5-(3-Aminopropionamido)-2,4,6-triiodoisophthalic acid bis(2,3-dihydroxypropyl)diamide, yield: 26% of theory, m.p. 278°-281° (decomposition) from 2,4,6-triiodo-5-phthalimidopropionamidoisophthalic acid bis(2,3-dihydroxypropyl)diamide, m.p. 298°-300° (decomposition).

(d) 5-Aminoacetamido-2,4,6-triiodoisophthalic acid tetrakis(2-hydroxyethyl)diamide, yield: 44% of theory, m.p. 262°-263° (decomposition) from 2,4,6-triiodo-5-phthalimidoacetamidoisophthalic acid tetrakis(2-hydroxyethyl)diamide, m.p. 283°-285° (decomposition).

EXAMPLE 7

5-Aminoacetamido-2,4,6-triiodoisophthalic Acid Bis(N-methyl-2,3-dihydroxypropyl)diamide Salt of Iothalamic acid

| | |
|---|---|
| 5-Aminoacetamido-2,4,6-triiodoisophthalic acid bis(N-methyl-2,3-dihydroxypropyl)diamide | 394.3 g |
| 5-Acetamido-2,4,6-triiodoisophthalic acid monomethylamide (iothalamic acid) | 306.4 g |
| Calcium disodium edetate | 0.1 g |
| Double-distilled water ad | 1000 ml |

Before filling up to total volume, the solution is optionally adjusted to pH 6.5-7.5 by adding a small amount of the corresponding acid or base; the solution is filtered through a bacterial filter, dispensed, and sterilized. The solution contains 380 mg I/ml.

EXAMPLE 8

5-Aminoacetamido-2,4,6-triiodoisophthalic Acid Bis(N-methyl-2,3-dihydroxypropyl)diamide Salt of 5,5'-(3,6-Dioxaoctanedioyldiimino)-bis[2,4,6-triiodo-3-(2-methoxy-1-methylcarbamoylethyl)]isophthalamic Acid

| | |
|---|---|
| 5-Aminoacetamido-2,4,6-triiodoisophthalic acid bis(N-methyl-2,3-dihydroxypropyl)diamide | 39.4 g |
| 5,5'-(3,6-Dioxaoctanedioyldiimino)-bis[2,4,6-triiodo-3-(2-methoxy-1-methylcarbamoylethyl)]isophthalamic acid | 37.1 g |
| Calcium disodium edetate | 0.01 g |
| Double-distilled water ad | 100 ml |

Before filling up to total volume, the solution is optionally adjusted to pH 6.5-7.5 by adding a small amount of the corresponding acid or base; the solution is filtered through a bacterial filter, dispensed, and sterilized. The solution contains 380 mg I/ml.

EXAMPLE 9

2,4,6-Triiodo-5-methylaminoacetamidoisophthalic Acid Bis(N-methyl-2,3-dihydroxypropyl)diamide Salt of Iothalamic Acid

| | |
|---|---|
| 2,4,6-Triiodo-5-methylaminoacetamidoisophthalic acid bis(N-methyl-2,3-dihydroxypropyl)diamide | 31.7 g |
| 5-Acetamido-2,4,6-triiodoisophthalic acid monomethylamide (iothalamic acid) | 24.2 g |
| Calcium disodium edetate | 0.01 g |
| Double-distilled water ad | 100 ml |

Before filling up to total volume, the solution is optionally adjusted to pH 6.5-7.5 by adding a small amount of the corresponding acid or base; the solution is filtered through a bacterial filter, dispensed, and sterilized. The solution contains 300 mg I/ml.

EXAMPLE 10

5-Aminoacetamido-2,4,6-triiodoisophthalic Acid Bis(2-hydroxyethyl)diamide Salt of Iothalamic Acid

| | |
|---|---|
| 5-Aminoacetamido-2,4,6-triiodoisophthalic acid bis(2-hydroxyethyl)diamide | 27.7 g |
| 5-Acetamido-2,4,6-triiodoisophthalic acid monomethylamide (iothalamic acid) | 24.2 g |
| Calcium disodium edetate | 0.01 g |
| Double-distilled water ad | 100 ml |

Before filling up to total volume, the solution is optionally adjusted to a pH 6.5-7.5 by adding a small quantity of the corresponding acid or base. Subsequently the solution is filtered over a bacterial filter, dispensed, and sterilized. The solution contains 300 mg I/ml of solution.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 5-amino-2,4,6-triiodoisophthalic acid bisamide of the formula

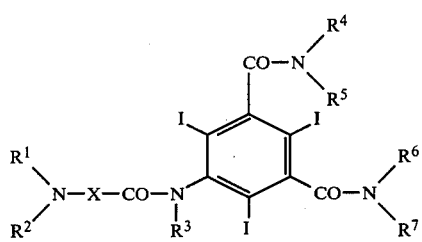

wherein
X is $C_{1-5}$-alkylene, optionally substituted by hydroxy, methoxy or amino;
$R^1$ is hydroxy or $C_{1-4}$-alkyl;
$R^2$ is hydrogen, $C_{1-4}$-alkyl, or $C_{2-4}$-alkyl substituted by 1–3 OH groups;
$R^3$ is hydrogen, $C_{1-4}$-alkyl, or $C_{2-4}$ alkyl substituted by 1–3 OH groups;
$R^4$ is hydrogen, $C_{1-4}$-alkyl, or $C_{2-4}$-alkyl substituted by 1–4 OH groups;
$R^5$ is $C_{2-4}$-alkyl substituted by 1–3 OH groups;
$R^6$ is hydrogen, $C_{1-4}$-alkyl or $C_{2-4}$-alkyl substituted by 1–3 OH groups; and
$R^7$ is $C_{2-4}$-alkyl substituted by 1–3 OH groups,
or a salt thereof with an acid which is an opaquing agent for x-ray contrast media.

2. A compound of claim 1 which is a salt of an acid which is an opaquing agent for x-ray contrast media.

3. A compound of claim 1 wherein the non-hydroxylated alkyl moieties are of 1–2 C atoms and the hydroxyalkyl groups are of 2–3 C atoms and contain 2 OH groups.

4. 5-Aminoacetamido-2,4,6-triiodoisophthalic acid bis(2-hydroxyethyl)diamide, a compound of claim 1.

5. 5-Aminoacetamido-2,4,6-triiodoisophthalic acid bis(N-methyl-2,3-dihydroxypropyl)diamide, a compound of claim 1.

6. A 5-Aminoacetamido-2,4,6-triiodoisophthalic acid bis(2-hydroxyethyl)diamide salt of iothalamic acid, a compound of claim 1.

7. A 5-Aminoacetamido-2,4,6-triiodoisophthalic acid bis(N-methyl-2,3-dihydroxypropyl)diamide salt of iothalamic acid, a compound of claim 1.

8. 5-Aminoacetamido-2,4,6-triiodoisophthalic acid bis(N-methyl-2,3-dihydroxypropyl)diamide salt of amidotrizoic acid, a compound of claim 1.

9. A pharmaceutical x-ray contrast medium comprising a radioopaque effective amount of a compound of claim 1 and a pharmaceutically acceptable carrier.

10. The x-ray contrast medium of claim 9 wherein the radioopaque agent is a salt of an acid which is an opaquing agent for x-ray contrast media.

11. A method of x-ray visualization of a body part of a host which comprises prior to the taking of x-rays, administering to the host an amount of a compound of claim 1 effective as an x-ray opaque agent for the body part to be visualized and, subsequently, taking x-rays of the body part to be visualized.

12. A method of rendering a body part of a host visualizable by x-rays, which comprises administering to the host an amount of a compound of claim 1 effective as an x-ray opaque agent for the body part to be visualized.

* * * * *